US009554990B2

United States Patent
Hara et al.

(10) Patent No.: US 9,554,990 B2
(45) Date of Patent: Jan. 31, 2017

(54) CHOLECYSTOKININ SECRETION-PROMOTING COMPOSITION

(71) Applicant: J-OIL MILLS, INC., Tokyo (JP)

(72) Inventors: Hiroshi Hara, Hokkaido (JP); Tohru Hira, Hokkaido (JP); Chigusa Nishiyama, Tokyo (JP); Noriko Tokura, Tokyo (JP); Takatoshi Yamashita, Tokyo (JP); Jun Imagi, Tokyo (JP)

(73) Assignee: J-Oil Mills, Inc., Tokyo (JP)

( * ) Notice: Subject to any disclaimer, the term of this patent is extended or adjusted under 35 U.S.C. 154(b) by 0 days.

(21) Appl. No.: 14/984,752

(22) Filed: Dec. 30, 2015

(65) Prior Publication Data

US 2016/0106668 A1    Apr. 21, 2016

Related U.S. Application Data

(63) Continuation of application No. 14/630,911, filed on Feb. 25, 2015, now abandoned, which is a continuation of application No. PCT/JP2013/068827, filed on Jul. 10, 2013.

(30) Foreign Application Priority Data

Sep. 14, 2012   (JP) ................. 2012-202450

(51) Int. Cl.
| | | |
|---|---|---|
| *A61K 31/11* | (2006.01) | |
| *A61K 31/19* | (2006.01) | |
| *C07C 47/21* | (2006.01) | |
| *A61K 9/00* | (2006.01) | |

(52) U.S. Cl.
CPC ............. *A61K 9/0056* (2013.01); *A23L 33/10* (2016.08); *A61K 31/11* (2013.01); *A61K 31/19* (2013.01); *C07C 47/21* (2013.01); *A23V 2002/00* (2013.01)

(58) Field of Classification Search
CPC ...... A61K 9/0056; A61K 31/11; A61K 31/19; C07C 47/21; A23L 33/10
USPC ....................................................... 514/703
See application file for complete search history.

(56) References Cited

U.S. PATENT DOCUMENTS

| | | |
|---|---|---|
| 2007/0066819 A1 | 3/2007 | Abdel-Magid et al. |
| 2007/0160737 A1 | 7/2007 | Colliver et al. |
| 2012/0052177 A1 | 3/2012 | Takakura et al. |

FOREIGN PATENT DOCUMENTS

| | | |
|---|---|---|
| JP | H0368597 A | 3/1991 |
| JP | H2004010569 A | 1/2004 |
| JP | 2004135522 A | 5/2004 |
| JP | H2007230978 A | 9/2007 |
| JP | 2009508865 A | 3/2009 |
| JP | 2009084191 A | 4/2009 |
| JP | 2009523016 A | 6/2009 |
| JP | 2012152173 A | 8/2012 |
| WO | 2010110493 A1 | 9/2010 |

OTHER PUBLICATIONS

International Search Report in counterpart International Application No. PCT/JP2013/068827, mailed Aug. 27, 2013.
Eiyo Kino Kagaku, (Nutritional Biochemistry), p. 42, (edited by Eiyo Kino Kagaku Kenkyukai, Asakura Publishing Co., Ltd., published in 1996). (with English language abstract).
Sufian. Kaosar Niaz B., et al., Soybean Conglycinin Bromelain Hydrolysate Stimulates Cholecystokinin Secretion by Enteroendocrine STC-1 Cells to Suppress the Appetite of Rats under Meal-Feeding Conditions, Biosci. Biotechnol. Biochem., 75(5), 848-853, 2011.
Hira. T., et al., Acute effect of soybean beta-conglycinin hydrolysate ingestion on appetite sensations in healthy humans, Appetite, 57(3), 765-768, 2011.
http://www.naro.affrc.go.jp/brain/ibunya/files/2006_7syokuyoku. pdf (with English language abstract).
Kim et al. Journal of Medicinal Food, 2011, 14(6), 573-583.

*Primary Examiner* — Yevegeny Valenrod
(74) *Attorney, Agent, or Firm* — Edell, Shapiro & Finnan, LLC

(57) ABSTRACT

A method is provided to promote secretion of cholecystokinin (CCK) by administering an active component. The active component includes acrylic acid and/or an unsaturated aldehyde having a main chain of 4 to 12 carbon atoms having a double bond in at least position 2 or 4, where the main chain has 4 to 9 carbon atoms when there is a double bond in only position 2, and the main chain has 9 to 12 carbon atoms when there is a double bond in only position 4. The cholecystokinin secretion-promoting composition can be used as an appetite suppressant. By adding this cholecystokinin secretion-promoting composition to food, appetite-suppressing food products can be provided.

18 Claims, No Drawings

CHOLECYSTOKININ SECRETION-PROMOTING COMPOSITION

TECHNICAL FIELD

The present invention relates to a cholecystokinin secretion-promoting composition, more specifically, a cholecystokinin secretion-promoting composition useful as an appetite suppressant.

BACKGROUND

The term "obesity" refers to a state of having a larger body weight or a state of having an excessive accumulation of body fat compared to a normal state. Obesity is a contemporary lifestyle disease caused by biased dietary habits, lack of exercise, or lack of sleep. Obesity caused by a metabolic disorder or an endocrine disease is called symptomatic obesity. Either obesity can be a risk factor of diseases such as hyperlipidemia, hypercholesterolemia, hypertriglyceridemia, hypertension, arteriosclerosis, ischemic heart disease, stroke, and arteriosclerosis obliterans. Accordingly, prophylaxis or treatment of obesity can be an effective means for preventing these diseases.

Cholecystokinin (hereinafter, referred to as CCK) is a gastrointestinal hormone secreted from the duodenal mucosal cells by ingestion of a lipid, protein, or other nutrients. This hormone is known to accelerate the enzyme secretion from the pancreas, to contract the gallbladder, and to delay the transfer of gastric contents to the duodenum by closing the pylorus of the stomach (Non-Patent Literature 1). This hormone also directly acts on the central nervous system to suppress the appetite. Thus, the hormone has a physiological function of inducing a feeling of fullness.

By focusing on the physiological effects of CCK, materials having a CCK secretion stimulating activity have been searched, and the uses of the materials have been developed. For example, Patent Literature 1 (Arginine-containing peptide having a cholecystokinin secretion-stimulating activity and food containing the peptide) discloses that a pepsin digestion product of soybean β-conglycinin promotes the CCK-secreting activity in rats to reduce the food intake and that the soybean β-conglycinin is used in a food intake-suppressing food. Non-Patent Literatures 2 and 3 ("Soybean β-Conglycinin Bromelain Hydrolysate Stimulates Cholecystokinin Secretion by Enteroendocrine STC-1 Cells to Suppress the Appetite of Rats under Meal-Feeding Conditions" and "Acute effect of soybean beta-conglycinin hydrolysate ingestion on appetite sensations in healthy humans") report on that a bromelain hydrolysate of soybean β-conglycinin having a CCK secretion-promoting action suppresses the appetite of rats and human beings. Non-Patent Literature 4 (Development of peptide regulating appetite by controlling a gastrointestinal hormone with high safety) reports on a food containing a bromelain digestion product or peptide of β-conglycinin.

Patent Literature 2 (Composition containing pork-derived peptide having a food intake-suppressing action) discloses a composition containing a peptide having a cholecystokinin secretion-stimulating activity or food intake-suppressing activity prepared by digesting pork or pork-derived protein with pepsin on the basis that the pig-derived peptide promotes CCK secretion and reduces the food intake of rats.

Patent Literature 3 (Pharmacological composition for suppressing appetite) discloses a pharmacological composition for suppressing appetite containing an ingredient showing a cholecystokinin secretion-stimulating action prepared from yeast. This ingredient is low in calorie and has high heat resistance and high enzymolysis resistance.

The list of patent literature and non-patent literature documents as described herein is as follows:

PATENT LITERATURE

Patent Literature 1: Japanese Patent Laid-Open No. 2004-10569
Patent Literature 2: Japanese Patent Laid-Open No. 2007-230978
Patent Literature 3: Japanese Patent Laid-Open No. 2009-84191

NON-PATENT LITERATURE

Non-Patent Literature 1: Eiyo Kino Kagaku (Nutritional Biochemistry), p. 42, (edited by Eiyo Kino Kagaku Kenkyukai, Asakura Publishing Co., Ltd., published in 1996)
Non-Patent Literature 2: Biosci. Biotechnol. Biochem., 75(5), 848-853, 2011
Non-Patent Literature 3: Appetite, 57(3), 765-768, 2011
Non-Patent Literature 4: http://www.naro.affrc.go.jp/brain/ibunya/files/2006_7syokuyoku.pdf

SUMMARY

It has been demonstrated that there are CCK secretion-promoting materials, such as a degradation product of β-conglycinin and a pig-derived peptide, and that these materials cause advantageous effects, such as a delay in the excretion of gastric contents, a reduction in food intake, and an increase in the feeling of fullness, in animals including human beings.

Accordingly, it is an object of the present invention to search a new orally ingestible CCK secretion-promoting material and to provide a use of the material.

During studies on the mechanism of promoting the secretion of CCK in cultured cells by food ingredients, the present inventors have surprisingly found that acrylic acid and specific unsaturated aldehydes have a CCK secretion-stimulating activity and have accomplished the present invention. That is, the present invention provides a cholecystokinin secretion-promoting composition (hereinafter, referred to as CCK secretion-promoting agent) as an active component, acrylic acid and/or an unsaturated aldehyde having a main chain of 4 to 12 carbon atoms having a double bond in at least position 2 or 4, wherein the main chain has 4 to 9 carbon atoms if there is a double bond in only position 2, and the main chain has 9 to 12 carbon atoms if there is a double bond in only position 4. Throughout the specification, the location of a double bond is numbered in accordance with the IUPAC nomenclature.

The secretion of cholecystokinin produced by I cells in the small intestine is physiologically promoted by peptides, amino acids, and fatty acids in the duodenum. For example, peptides (such as degradation products of β-conglycinin), proteins (whey and casein), fatty acids, and calcium are conventionally known to promote the secretion of CCK. However, it is quite a surprise that the unsaturated aldehydes and other materials specified by the present invention have a CCK secretion-stimulating activity.

The unsaturated aldehyde is preferably selected from the group consisting of di-unsaturated aldehydes having 4 to 12 main-chain carbon atoms and having double bonds in positions 2 and 4, mono-unsaturated aldehydes having 4 to 9 main-chain carbon atoms and having a double bond in position 2, and mono-unsaturated aldehydes having 9 to 12 main-chain carbon atoms and having a double bond in position 4.

The CCK secretion-promoting agent preferably comprises the unsaturated aldehyde having a double bond in position 2.

The CCK secretion-promoting agent preferably comprises the unsaturated aldehyde having double bonds in positions 2 and 4. The unsaturated aldehydes are preferably in trans conformations.

The CCK secretion-promoting agent preferably comprises the unsaturated aldehyde having two double bonds and the unsaturated aldehyde having one double bond, or comprises the unsaturated aldehyde having two different double bonds. In particular, the unsaturated aldehyde having one double bond is preferably trans-2-octenal.

The present invention also provides an appetite suppressant including the CCK secretion-promoting agent.

The present invention also provides an appetite-suppressing food product including the CCK secretion-promoting agent.

DETAILED DESCRIPTION

The present invention relates to a novel CCK secretion-promoting agent containing a specific unsaturated aldehyde as an active ingredient. Some examples of the unsaturated aldehyde used in the present invention have been confirmed to be safe as food additives. These unsaturated aldehydes are inexpensively available and can be easily processed into a solution or a solid. Thus, the unsaturated aldehydes are superior to conventional CCK secretion-promoting materials in these points.

Oral ingestion of the CCK secretion-promoting agent of the present invention promotes the activity of secreting cholecystokinin, resulting in a reduction in food intake and also a decrease in the sensation of hunger. Accordingly, the CCK secretion-promoting agent of the present invention can be used as, for example, an appetite suppressant, hyperphagia preventive agent, or obesity preventive agent.

The present invention can also provide an appetite-suppressing food product that induces a feeling of fullness with a small amount thereof. The appetite-suppressing food product can be prepared by adding a cholecystokinin secretion-promoting composition of the present invention to a foodstuff.

The CCK secretion-promoting agent of the present invention comprises acrylic acid and/or an unsaturated aldehyde having 4 to 12 main-chain carbon atoms and a double bond in at least position 2 or 4. It has been revealed that acrylic acid and/or a specific unsaturated aldehyde used in the present invention has a high CCK-secreting activity, whereas saturated aldehydes, saturated or unsaturated alcohols, saturated fatty acids, unsaturated fatty acid excluding acrylic acid, and saturated or unsaturated hydrocarbons have a low CCK secretion-stimulating activity.

The mono-unsaturated aldehyde having a double bond in only position 2 has 4 to 9 main-chain carbon atoms. If the number of carbon atoms in the main chain is at least 10, the CCK-secreting activity decreases. The mono-unsaturated aldehyde having a double bond in only position 4 has 9 to 12 main-chain carbon atoms. If the number of carbon atoms in the main chain is not more than 8, the CCK-secreting activity decreases.

Although an unsaturated aldehyde having three main-chain carbon atoms and having a double bond in position 2, propenal, also has a CCK-secreting activity, Globally Harmonized System of Classification and Labeling of Chemicals (GHS) classifies propenal in class 2 of acute toxicity (the swallowing of it endangers the life). Thus, propenal is believed to be highly toxic and is inadequate as a CCK secretion-promoting agent that is ingested to human beings. Some unsaturated aldehydes having more than 12 main-chain carbon atoms are solid at ordinary temperature and are predicted to cause separation or precipitation when they are used in liquid formulations or foods. Thus, such unsaturated aldehydes may be restricted in the use. In also unsaturated aldehydes having a double bond in a position other than positions 2 and 4, the CCK-secreting activity is low.

Examples of the CCK secretion-promoting agent include trans,trans-2,4-hexadienal, trans,trans-2,4-heptadienal, trans,trans-2,4-nonadienal, trans,trans-2,4-decadienal, trans,trans-2,4-dodecadienal, 2,3-butadienal, 2,4-pentadienal, 3,4-pentadienal, 2,7-octadienal, 2,6-octadienal, 2,4-octadienal, 2,6-nonadienal, 4,7-decadienal, 2,4-undecadienal, 2,6-dodecadienal, 3,7-dimethyl-2,6-nonadienal, trans-2-methyl-2,6-heptadienal, 2,4-dimethyl-2,6-heptadienal, 3,6-dimethyl-2,5-heptadienal, 3,7-dimethyl-2,6-octadienal, 3,7-dimethyl-2,7-octadienal, 2,4-diethyl-2,6-heptadienal, 3,4,8-trimethyl-2,7-nonadienal, 5,9-dimethyl-4,9-decadienal, 4,8-dimethyl-4,9-decadienal, 5,9-dimethyl-4,8-decadienal, trans-2-methyl-6-methylene-2,7-octadienal, 4,5-hexadienal, 4,7-undecadienal, trans-2-butenal, trans-2-heptenal, trans-2-octenal, trans-2-nonenal, trans-2-pentenal, 3-methyl-2-butenal, trans-2-methyl-2-butenal, 2-ethyl-2-butenal, 4-methyl-2-pentenal, trans-2-methyl-2-pentenal, 2-methyl-2-octenal, 2-propyl-2-heptenal, 3-propyl-2-heptenal, 4-(2,5-dimethyl-cyclohexylidene)-2-butenal, 2-butyl-2-octenal, 5-(methylthio)-2-[(methylthio)methyl]-2-pentenal, 4-methyl-2-[(methylthio)methyl]-2-hexenal, 5-methyl-2-[(methylthio)methyl]-2-hexenal, 4-methyl-2-[(methylthio)methyl]-2-pentenal, 2-[(methylthio)methyl]-2-butenal, 2-ethyl-2-hexenal, 2-butyl-2-octenal, trans-4-decenal, cis-4-decenal, 4-nonenal, 4-dodecenal, 4-undecenal, 2-methyl-4-undecenal, 2-methyl-4-dodecenal, 2,4,6-octatrienal, 5,9-dimethyl-2,4,8-decatrienal, 2,4,6-nonatrienal, 2,4,8-undecatrienal, 2,4,6,8-undecatetraenal, 2,4,6,8-nonatetraenal, 2,4,6,8-decatetraenal, 2,4,6,8,10-undecapentaenal, and 2,4,6,8,10-dodecapentaenal.

The unsaturated aldehyde is preferably selected from the group consisting of di-unsaturated aldehydes having 4 to 12 main-chain carbon atoms and having double bonds in positions 2 and 4, mono-unsaturated aldehydes having 4 to 9 main-chain carbon atoms and having a double bond in position 2, and mono-unsaturated aldehydes having 9 to 12 main-chain carbon atoms and having a double bond in position 4. Examples of such an unsaturated aldehyde include trans,trans-2,4-hexadienal, trans,trans-2,4-heptadienal, trans,trans-2,4-nonadienal, trans,trans-2,4-decadienal, trans,trans-2,4-dodecadienal, 2-butenal, trans-2-heptenal, trans-2-octenal, trans-2-nonenal, trans-4-decenal, and cis-4-decenal.

The CCK secretion-promoting agent of the present invention preferably contains an unsaturated aldehyde having a double bond in position 2. Examples of such an unsaturated aldehyde include trans,trans-2,4-hexadienal, trans,trans-2,4-heptadienal, trans,trans-2,4-nonadienal, trans,trans-2,4-decadienal, trans,trans-2,4-dodecadienal, 2-butenal (crotonaldehyde), trans-2-heptenal, trans-2-octenal, and trans-2-nonenal.

The CCK secretion-promoting agent containing an unsaturated aldehyde having double bonds in positions 2 and 4 has a higher CCK-secreting activity and is particularly preferred. Examples of such an unsaturated aldehyde include trans,trans-2,4-hexadienal, trans,trans-2,4-heptadienal, trans,trans-2,4-nonadienal, trans-trans-2,4-decadienal, and trans,trans-2,4-dodecadienal.

The unsaturated aldehyde is preferably in a trans conformation.

The CCK secretion-promoting agent preferably contains an unsaturated aldehyde having two double bonds and an unsaturated aldehyde having one double bond or contains two different unsaturated aldehydes having two double bonds. It has been revealed that the combination of two or more different unsaturated aldehydes synergistically promotes the activity of secreting cholecystokinin. The unsaturated aldehyde having only one double bond preferably has eight or less carbon atoms and is more preferably trans-2-octenal. The unsaturated aldehyde having two double bonds is preferably trans,trans-2,4-hexadienal, trans,trans-2,4-heptadienal, or trans,trans-2,4-decadienal. In the CCK secretion-promoting agent containing two different unsaturated aldehydes having two double bonds, one of the unsaturated aldehydes is preferably trans,trans-2,4-heptadienal.

The CCK secretion-promoting agent of the present invention induces, for example, a delay in the excretion of gastric contents, a reduction in food intake (appetite), a decrease in the sensation of hunger, or an increase in the feeling of fullness in animals including human beings, as in the conventional cholecystokinin-secreting activity. Accordingly, examples of the use of the CCK secretion-promoting agent of the present invention include appetite suppressants, hyperphagia preventive or therapeutic agents, and obesity preventive or therapeutic agents (hereinafter, referred to as appetite suppressant, etc.).

The CCK secretion-promoting agent, the appetite suppressant, etc. of the present invention can be provided as drugs or functional foods. The content of the unsaturated aldehyde in the CCK secretion-promoting agent or the appetite suppressant, etc. is usually 0.005% to 60% by weight, preferably 0.05% to 30% by weight.

The CCK secretion-promoting agent and other agents of the present invention can contain pharmacologically or bromatologically acceptable other additives within a range that does not impair the effects of the present invention, in addition to the unsaturated aldehyde as an active ingredient. Examples of such additives include excipients such as corn starch, crystalline cellulose, and lactose; disintegrators such as starch, sodium alginate, gelatin, calcium carbonate, and calcium citrate; binding agents such as methyl cellulose and its salts, ethyl cellulose, gum arabic, and gelatin; lubricants such as talc, magnesium stearate, polyethylene glycol, and hydrogenated vegetable oils; xanthine derivatives; pH adjusters; cooling agents; suspending agents; viscous agents; solubilizers; antioxidants; coating agents; plasticizers; surfactants; water; alcohols; water-soluble polymers; sweeteners such as fructose, glucose, and sorbitol; corrigents; acidifiers such as citric acid; flavoring agents; coloring agents; vitamins; minerals; and lipids.

The CCK secretion-promoting agent and other agents of the present invention may be in any form. Examples of the form include solid formulations such as powders, granules, capsules, pills, tablets, chewable tablets, and drops; and liquid formulations such as drinkable preparations, liquid agents, suspensions, emulsions, syrups, and dry syrups.

The CCK secretion-promoting agent and other agents of the present invention may be administered in any route. In the case of a drug, the drug may be administered orally or parenterally (e.g., intravenous injection, intramuscular injection, subcutaneous injection, intraperitoneal administration, rectal administration, or transdermal administration).

Since the mechanism of the action of CCK is a delay of the transfer of gastric contents to the duodenum by closing the pylorus of the stomach, the CCK secretion-promoting agent and other agents of the present invention are desirably ingested before foods reach the duodenum. As shown by the cell test described below, since the CCK secretion-promoting agent produces the effect within 60 minutes after the ingestion, specifically, the CCK secretion-promoting agent and other agents of the present invention is preferably ingested before or during the meal.

In the case of using the CCK secretion-promoting agent and other agents of the present invention as drugs, the dosage varies depending on the age, body weight, and anamnesis (e.g., obesity) of a patient to whom the agent is administered. Specifically, the daily dosage of the unsaturated aldehyde is usually 0.5 to 10 mg/kg of body weight, preferably 1 to 5 mg/kg of body weight, for an adult.

In the case of using the CCK secretion-promoting agent and other agents of the present invention as functional foods, the ingestion amount varies depending on the age, body weight, and anamnesis (e.g., obesity) of a subject who ingests the agent. Specifically, the daily ingestion of the unsaturated aldehyde is usually 0.5 to 10 mg/kg of body weight, preferably 1 to 5 mg/kg of body weight, for an adult.

The present invention also provides an appetite-suppressing food product containing the CCK secretion-promoting agent. Examples of the food include feeds for pets. A food containing the CCK secretion-promoting agent of the present invention can suppress food ingestion. Examples of the food include, but not limited to, common processed foods and drinks, for example, side dishes such as salads, fried foods, tofu, and konnyaku; soups; bread, rice, and noodles; confectionery such as cookies, muffins, cakes, chips, snack confectionery, chocolates, jellies, puddings, chewing gum, and candies; dairy products such as yogurt and milk; fish meat pastes such as ham, sausages, and boiled fish pastes; drinks such as coffee, juices, and sports beverages; and flavorings such as dressings, soy sauce, and sauces.

The amount of the unsaturated aldehyde in an appetite-suppressing food product containing the CCK secretion-promoting agent is preferably 0.001% to 0.03% by weight, preferably 0.003% to 0.015% by weight.

EXAMPLES

The present invention will now be described in more detail by means of Examples according to the present invention and Comparative Examples, but is not limited to the following examples.

Examples 1 to 12

1-1. Preparation of Test Material

As shown in Table 1, aldehydes having 3 to 13 main-chain carbon atoms and having 0 to 2 double bonds in the main chain, ketones, alcohols, fatty acids, and hydrocarbons were prepared. As a condition for maximizing the secretion amount of CCK in a cell test system, 70 mM KCl (positive control) causing hormone release by depolarization was prepared.

Since the number of materials that can be tested at once is restricted, the test materials were divided into five groups as shown in Table 1. In order to solve the discontinuity between experimental groups, every group included trans, trans-2,4-decadienal. Each test material was tested three times, and the average value of the results was calculated.

TABLE 1

| Experimental group | Test material |
|---|---|
| 1 | trans,trans-2,4-hexadienal, trans,trans-2,4-heptadienal, trans,trans-2,4-nonadienal, trans,trans-2,4-decadienal, trans-2-butenal (crotonaldehyde), trans-2-heptenal, butanal (butyraldehyde), and nonanal |
| 2 | trans,trans-2,4-decadienal, trans,trans-2,4-dodecadienal, trans-4-decenal, cis-4-decenal, decanal, undecanal, dodecanal, tridecanal, trans-2-decenal, cis-4-heptenal, and cis-7-decenal |
| 3 | trans,trans-2,4-decadienal, trans-2-nonenal, octanal, trans-2-undecenal, trans-2-dodecenal, cis-6-nonenal, and trans-10-undecenal |
| 4 | trans,trans-2,4-decadienal, trans-2-octenal, cis-4-decenal, acrylic acid, 2-propen-1-ol, trans-2-octen-1-ol, cis-4-decen-1-ol, and trans-2-octenoic acid |
| 5 | trans,trans-2,4-decadienal, octanal, decanal, dodecanal, tridecanal, 1-octanol, n-decyl alcohol, dodecyl alcohol, n-tridecyl alcohol, trans-3-decen-2-one, n-octanoic acid, decanoic acid, lauric acid, n-tridecanoic acid, decane, cis-2-decene, and trans,trans-1,9-decadiene |

1-2. Process of Preparing Evaluation Solution

The test materials were each dissolved in ethanol, and each solution was diluted with Hepes buffer (140 mM NaCl, 4.5 mM KCl, 20 mM Hepes, 1.2 mM $CaCl_2$, 1.2 mM $MgCl_2$, and 10 mM D-glucose, pH 7.4) to give a 0.1 vol % ethanol solution, which was used as the evaluation solution.

1-3. Confirmation Test of CCK Secretion-Stimulating Activity

Mouse intestinal CCK-producing cell line STC-1 was cultured in a 48-well plate for two to three days until subconfluent in a Dulbecco's modified Eagle's medium containing 10% bovine fetal serum at 37° C. in the presence of 5% $CO_2$. After the wells were washed with Hepes buffer, 100 μL of the evaluation solution containing 100 μM of a test material was added to a well, followed by incubation at 37° C. for 60 minutes. The supernatant was collected and was centrifuged (800×g, 5 min, 4° C.) to precipitate the exfoliated cells. The resulting supernatant (80 μL) was collected and was cryopreserved. The concentration of CCK in the supernatant was measured with a commercially available enzyme immunoassay kit (manufactured by Phoenix Pharmaceuticals, Inc.).

The secretion amount of CCK varied from 10 to 30 pM among the tests of a vehicle (i.e., a blank). The secretion amounts of CCK in the tests for test materials (100 μM) of Examples 1 to 12 reached 30 to 60 pM and were always two to three times that by the vehicle, whereas the secretion amounts of CCK in the tests for test materials of Comparative Examples were equivalent to that by the vehicle or lower than that by the vehicle in some cases. Thus, it was demonstrated that acrylic acid and the specific unsaturated aldehydes used in Examples have a CCK secretion-stimulating activity.

In order to investigate the change in the secretion amount of CCK by addition of a test material to the cells in a general condition, a value obtained by subtracting the measured value of the vehicle from the measured value of a sample was used as the true value, and the score of the CCK secretion-stimulating activity was determined by dividing the true value by the value of 70 mM KCl as a control. The variance was analyzed for each experimental group. The difference in variance between an experimental group and the vehicle was examined for determining whether there was a significant difference (P<0.05). The results are shown in Tables 2A and 2B.

TABLE 2A

| | Name of ingredient | Class | Number of carbon atoms | Double bond Number | Position Position 2 | Position 4 | Others | Structure | CCK secretion-promoting activity Score | Significant difference from vehicle Group 1 | Group 2 | Group 3 | Group 4 | Group 5 |
|---|---|---|---|---|---|---|---|---|---|---|---|---|---|---|
| Control | 70 mM KCl | — | — | — | — | — | — | — | 1 | | | | | |
| Example 1 | trans,trans-2,4-hexadienal | aldehyde | 6 | 2 | ○ | ○ | | trans | 0.840 | * | | | | |
| Example 2 | trans,trans-2,4-heptadienal | aldehyde | 7 | 2 | ○ | ○ | | trans | 0.885 | * | | | | |
| Example 3 | trans,trans-2,4-nonadienal | aldehyde | 9 | 2 | ○ | ○ | | trans | 0.975 | * | | | | |
| Example 4 | trans,trans-2,4-decadienal | aldehyde | 10 | 2 | ○ | ○ | | trans | 1.088 | * | * | * | * | * |
| Example 5 | trans,trans-2,4-dodecadienal | aldehyde | 12 | 2 | ○ | ○ | | trans | 0.720 | | * | | | |
| Example 6 | trans-2-butenal (crotonaldehyde) | aldehyde | 4 | 1 | ○ | | | trans | 0.644 | * | | | | |
| Example 7 | trans-2-heptenal | aldehyde | 7 | 1 | ○ | | | trans | 0.624 | * | | | | |
| Example 8 | trans-2-octenal | aldehyde | 8 | 1 | ○ | | | trans | 0.698 | | | | * | |
| Example 9 | trans-2-nonenal | aldehyde | 9 | 1 | ○ | | | trans | 0.491 | | | — | | |
| Example 10 | trans-4-decenal | aldehyde | 10 | 1 | | ○ | | trans | 0.441 | | | — | | |
| Example 11 | cis-4-decenal | aldehyde | 10 | 1 | | ○ | | cis | 0.377 | | | — | | — |
| Example 12 | acrylic acid | fatty acid | 3 | 1 | ○ | | | trans | 0.957 | | | | * | |

*: A significant difference (P < 0.05) was found

—: No significant difference was found

TABLE 2B

| Name of ingredient | Class | Number of carbon atoms | Double bond Number | Position Position 2 | Position 4 | Others | Structure | CCK secretion-promoting activity Score | Significant difference from vehicle Group 1 | Group 2 | Group 3 | Group 4 | Group 5 |
|---|---|---|---|---|---|---|---|---|---|---|---|---|---|
| Control 70 mM KCl | — | — | — | — | — | — | — | 1 | | | | | |
| Comparative Example 1 butanal (butyraldehyde) | aldehyde | 4 | 0 | | | | | 0.017 | — | | | | |
| Comparative Example 2 octanal | aldehyde | 8 | 0 | | | | | −0.004 | | | — | | — |
| Comparative Example 3 nonanal | aldehyde | 9 | 0 | | | | | −0.003 | — | | | | |
| Comparative Example 4 decanal | aldehyde | 10 | 0 | | | | | 0.042 | | — | | | — |
| Comparative Example 5 undecanal | aldehyde | 11 | 0 | | | | | 0.189 | — | | | | |
| Comparative Example 6 dodecanal | aldehyde | 12 | 0 | | | | | −0.093 | — | | | | — |
| Comparative Example 7 tridecanal | aldehyde | 13 | 0 | | | | | 0.049 | — | | | | — |
| Comparative Example 8 trans-2-decenal | aldehyde | 10 | 1 | ○ | | | trans | 0.046 | — | | | | |
| Comparative Example 9 trans-2-undecenal | aldehyde | 11 | 1 | ○ | | | trans | −0.137 | | | — | | |
| Comparative Example 10 trans-2-dodecenal | aldehyde | 12 | 1 | ○ | | | trans | −0.319 | | | — | | |
| Comparative Example 11 cis-4-heptenal | aldehyde | 8 | 1 | | ○ | | cis | −0.001 | | | — | | |
| Comparative Example 12 cis-6-nonenal | aldehyde | 9 | 1 | | | position 6 | cis | −0.648 | | | — | | |
| Comparative Example 13 cis-7-decenal | aldehyde | 10 | 1 | | | position 7 | cis | 0.274 | | | — | | |
| Comparative Example 14 trans-10-undecenal | aldehyde | 11 | 1 | | | position 10 | trans | −0.458 | | | — | | |
| Comparative Example 15 2-propen-1-ol | alcohol | 3 | 1 | ○ | | | | 0.557 | | | | — | |
| Comparative Example 16 trans-2-octen-1-ol | alcohol | 8 | 1 | ○ | | | trans | 0.321 | | | | — | |
| Comparative Example 17 cis-4-decen-1-ol | alcohol | 10 | 1 | | ○ | | cis | −0.171 | | | | — | |
| Comparative Example 18 1-octanol | alcohol | 8 | 0 | | | | | −0.134 | | | | | — |
| Comparative Example 19 n-decyl alcohol | alcohol | 10 | 0 | | | | | 0.070 | | | | | — |
| Comparative Example 20 dodecyl alcohol | alcohol | 12 | 0 | | | | | −0.304 | | | | | — |
| Comparative Example 21 n-tridecyl alcohol | alcohol | 13 | 0 | | | | | −0.225 | | | | | — |
| Comparative Example 22 trans-3-decen-2-one | ketone | 10 | 1 | | | position 3 | trans | 0.169 | | | | | — |
| Comparative Example 23 trans-2-octenoic acid | fatty acid | 8 | 1 | ○ | | | trans | 0.146 | | | — | | |
| Comparative Example 24 n-octanoic acid | fatty acid | 8 | 0 | | | | | −0.140 | | | | | — |
| Comparative Example 25 decanoic acid | fatty acid | 10 | 0 | | | | | −0.207 | | | | | — |
| Comparative Example 26 lauric acid | fatty acid | 12 | 0 | | | | | −0.225 | | | | | — |
| Comparative Example 27 n-tridecanoic acid | fatty acid | 13 | 0 | | | | | −0.234 | | | | | — |
| Comparative Example 28 decane | hydrocarbon | 10 | 0 | | | | | −0.224 | | | | | — |
| Comparative Example 29 cis-2-decene | hydrocarbon | 10 | 1 | ○ | | | cis | −0.208 | | | | | — |
| Comparative Example 30 trans,trans-1,9-decadiene | hydrocarbon | 10 | 2 | | | positions 1, 9 | trans | −0.211 | | | | | — |

*: A significant difference (P < 0.05) was found
—: No significant difference was found Tables 2A and 2B revealed the following: A CCK secretion-stimulating activity was observed in unsaturated aldehydes of Examples 1 to 11 with significant differences. The comparison between Examples 1 to 11 and Comparative Examples 15 to 30 demonstrates that alcohols, fatty acids excluding acrylic acid, and hydrocarbons do not have a CCK secretion-stimulating activity, whereas aldehydes have a CCK secretion-stimulating activity. The comparison between Examples 1 to 11 and Comparative Examples 1 to 7 demonstrates that the aldehydes must be unsaturated aldehydes. The comparison between Examples 1 to 11 and Comparative Examples 12 to 14 demonstrates that a double bond must be present in at least position 2 or 4.

The comparison between Examples 6 to 9 and Comparative Examples 8 to 10 demonstrates that an unsaturated aldehyde having a double bond in only position 2 must have 9 or less main-chain carbon atoms. The comparison between Examples 10 to 11 and Comparative Example 11 demonstrates that an unsaturated aldehyde having a double bond in only position 4 must have 9 or more main-chain carbon atoms.

The comparison between Example 10 and Example 11 demonstrates that preferred unsaturated aldehydes are in trans conformations. The superiority of the trans conformation is also suggested in that the best results are obtained in Examples 1 to 5 all in trans conformations.

As shown in Examples 1 to 5, the excellent results regarding the CCK secretion-stimulating activity are observed in unsaturated aldehydes having double bonds in positions 2 and 4. In particular, the CCK secretion-stimulating activity of trans,trans-2,4-decadienal is the highest.

It has been confirmed in a cell test system of a conventional technology that an ingredient (e.g., a degradation product of β-conglycinin) showing a CCK-secreting activity suppresses appetite. Accordingly, it is obvious that the CCK secretion-promoting agent of the present invention also functions as an appetite suppressant.

Examples 13 to 23

Synergistic Effect of CCK Secretion-Stimulating Activity

Combinations of two different unsaturated aldehydes shown in Table 3 were evaluated for their CCK secretion-stimulating activity. The evaluation was performed as in Example 1 except that the concentrations of the two different test materials were each 50 μM (a half of the concentration in the test described in paragraph 1-3). The results are shown in Table 3.

TABLE 3

| | | | CCK secretion-promoting activity | |
|---|---|---|---|---|
| | Ingredient 1 | Ingredient 2 | Score | Significant difference from vehicle |
| Control | 70 mM KCl (100 μM) | | 1 | |
| Example 4 | trans,trans-2,4-decadienal (100 μM) | | 1.088 | * |
| Example 13 | trans,trans-2,4-decadienal | trans,trans-2,4-hexadienal | 0.492 | * |
| Example 14 | trans,trans-2,4-decadienal | trans,trans-2,4-heptadienal | 0.795 | * |
| Example 15 | trans,trans-2,4-decadienal | trans-2-octenal | 1.127 | * |
| Example 16 | trans,trans-2,4-decadienal | trans-2-nonenal | 0.594 | — |
| Example 17 | trans,trans-2,4-hexadienal | trans,trans-2,4-heptadienal | 0.934 | * |
| Example 18 | trans,trans-2,4-hexadienal | trans-2-octenal | 1.190 | * |
| Example 19 | trans,trans-2,4-hexadienal | trans-2-nonenal | 0.868 | * |
| Example 20 | trans,trans-2,4-heptadienal | trans-2-octenal | 1.383 | * |
| Example 21 | trans-2-octenal | trans-2-nonenal | 0.479 | — |

* A significant difference (P < 0.05) was found
—: No significant difference was found Table 3 demonstrates that the CCK-secreting activity is promoted by a combination of an unsaturated aldehyde having two double bonds and an unsaturated aldehyde having one double bond or by a combination of two different unsaturated aldehydes having two double bonds. It has been demonstrated that the CCK-secreting activity is highly promoted, in particular, by a combination of an unsaturated aldehyde having two double bonds and an unsaturated aldehyde having eight or less carbon atoms and one double bond. It has been demonstrated that the CCK-secreting activity is further highly promoted by a combination of an unsaturated aldehyde having double bonds in positions 2 and 4 and trans-2-octenal having a double bond in position 2.

The invention claimed is:

1. A method comprising administering to a human an amount of an active component effective to promote secretion of cholecystokinin (CCK) from enteroendocrine cells of the human, wherein the active component consists of acrylic acid and/or an unsaturated aldehyde having a main chain of 4 to 12 carbon atoms having a double bond in at least position 2 or 4, wherein the main chain has 4 to 9 carbon atoms when there is a double bond in only position 2, and the main chain has 9 to 12 carbon atoms when there is a double bond in only position 4.

2. The method of claim 1, wherein the active component comprises an unsaturated aldehyde selected from the group consisting of di-unsaturated aldehydes having 4 to 12 main-chain carbon atoms and having double bonds in positions 2 and 4, mono-unsaturated aldehydes having 4 to 9 main-chain carbon atoms and having a double bond in position 2, and mono-unsaturated aldehydes having 9 to 12 main-chain carbon atoms and having a double bond in position 4.

3. The method of claim 2, wherein the unsaturated aldehyde has a double bond in position 2.

4. The method of claim 2, wherein the unsaturated aldehyde has double bonds in positions 2 and 4.

5. The method of claim 2, wherein the active component comprises:
   one unsaturated aldehyde having two double bonds and another unsaturated aldehyde having one double bond; or
   two different unsaturated aldehydes each having two double bonds.

6. The method of claim 2, wherein the unsaturated aldehyde is in a trans conformation.

7. The method of claim 2, wherein the unsaturated aldehyde is trans-2-octenal.

8. The method of claim 2, further comprising administering a composition to the human including the active component, wherein the unsaturated aldehyde is provided within the composition in an amount of 0.005% to 60% by weight of the composition.

9. The method of claim 8, wherein the unsaturated aldehyde is provided within the composition in an amount of 0.05% to 30% by weight of the composition.

10. The method of claim 2, wherein the unsaturated aldehyde is administered to the human in a daily dosage of 0.5 to 10 mg/kg bodyweight of the human.

11. The method of claim 10, wherein the unsaturated aldehyde is administered to the human in a daily dosage of 1 to 5 mg/kg bodyweight of the human.

12. The method of claim 1, wherein the active component is administered to the human orally or parenterally.

13. The method of claim 12, wherein the active component is administered to the human in a solid formulation or a liquid formulation.

14. The method of claim 2, wherein the active component is administered orally to the human in an amount effective to suppress appetite in the human.

15. The method of claim 14, wherein the active component is provided within a food product for oral consumption by the human, and the amount of unsaturated aldehyde from the active component in the food product is 0.001% to 0.03% by weight of the food product.

16. The method of claim 15, wherein the amount of unsaturated aldehyde from the active component in the food product is 0.003% to 0.15% by weight of the food product.

17. The method of claim 14, wherein the active component is administered orally to the human before or during a meal ingested by the human.

18. The method of claim 17, wherein the active component is administered orally to the human within 60 minutes of the human ingesting the meal.

\* \* \* \* \*